(12) United States Patent
Lee et al.

(10) Patent No.: US 9,732,323 B2
(45) Date of Patent: Aug. 15, 2017

(54) METHODS FOR PRODUCING MATURE HEPATOCYTES

(75) Inventors: Oscar Kuang-Sheng Lee, Taipei (TW); Yu-Fan Chen, Taipei (TW); Chien-Yu Tseng, Taipei (TW)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 1093 days.

(21) Appl. No.: 13/619,893

(22) Filed: Sep. 14, 2012

(65) Prior Publication Data

US 2013/0259836 A1 Oct. 3, 2013

Related U.S. Application Data

(60) Provisional application No. 61/617,523, filed on Mar. 29, 2012.

(51) Int. Cl.
*C12N 5/071* (2010.01)
*A61K 35/407* (2015.01)

(52) U.S. Cl.
CPC ............ *C12N 5/067* (2013.01); *A61K 35/407* (2013.01); *C12N 2500/25* (2013.01); *C12N 2501/12* (2013.01); *C12N 2501/16* (2013.01); *C12N 2501/237* (2013.01); *C12N 2501/39* (2013.01); *C12N 2501/415* (2013.01); *C12N 2506/45* (2013.01)

(58) Field of Classification Search
CPC C12N 5/067; C12N 2500/25; C12N 2501/12; C12N 2501/16; C12N 2501/237; C12N 2501/39; C12N 2501/415; C12N 2506/45; A61K 35/407
See application file for complete search history.

(56) References Cited

U.S. PATENT DOCUMENTS

| | | |
|---|---|---|
| 2005/0037493 A1 | 2/2005 | Mandalam et al. |
| 2006/0205075 A1 | 9/2006 | Nakatsuji et al. |
| 2009/0136955 A1 | 5/2009 | Mandalam et al. |
| 2009/0317365 A1 | 12/2009 | Lee et al. |
| 2011/0311977 A1 | 12/2011 | Mandal et al. |
| 2012/0028354 A1 | 2/2012 | Lee et al. |
| 2012/0190059 A1* | 7/2012 | Deng ............... C12N 5/067 435/29 |

FOREIGN PATENT DOCUMENTS

WO WO/2011/009294 * 1/2011

OTHER PUBLICATIONS

Tayeb et al Hepatology, 2010, 51, 297-305.*
Chen et al Hepatology, Apr. 2012; 55(4):1193-203.*
Hay et al PNAS, 2008, 105, 34, 12301-12306.*
Hay et al Stem Cells, 2008;26:894-902.*
Y. F. Chen et al., "Rapid Generation of Mature Hepatocyte-Like Cells from Human Induced Pluripotent Stem Cells by an Efficient Three-Step Protocol" *Hepatology*, vol. 55, Issue 4, pp. 1193-1203, Apr. 2012.

* cited by examiner

*Primary Examiner* — Anoop Singh
(74) *Attorney, Agent, or Firm* — Muncy, Geissler, Olds & Lowe, P.C.

(57) ABSTRACT

The present invention describes an efficient and rapid protocol to generate hepatocyte cells from human induced pluripotent stem cells (iPSCs). According to the method, the iPS cells can be differentiated into functional hepatocyte cells in a short time course (less than 15-20 days). The iPSC-derived hepatocyte cells of the invention have a similar gene expression profile to mature hepatocytes. Moreover, the iPSC-derived hepatocyte cells is proved to rescue lethal fulminant hepatic failure in a non-obese diabetic severe combined immunodeficient mouse model. The rapid and efficient differentiation protocol for generation of iPSC-derived hepatocyte cells may offer an alternative option for treatment of liver diseases.

3 Claims, 13 Drawing Sheets

(9 of 13 Drawing Sheet(s) Filed in Color)

Fig.2(A) Day -4 to Day 0    Day 1 to Day 3    Day 4 to Day 7    Day 8 to Day 12
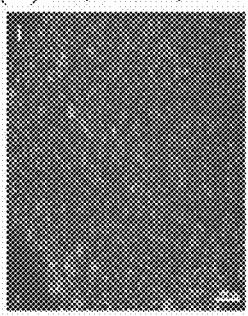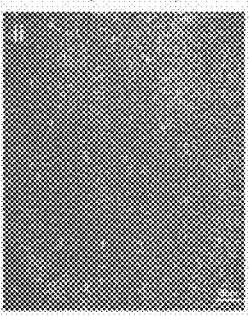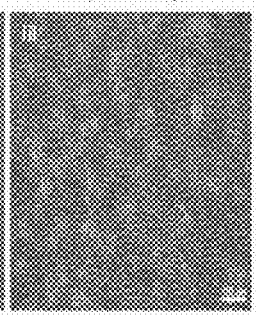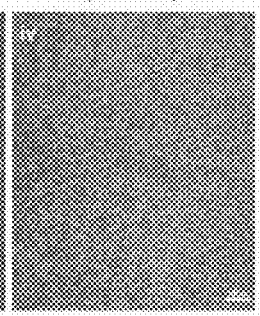
Fig.2(B)
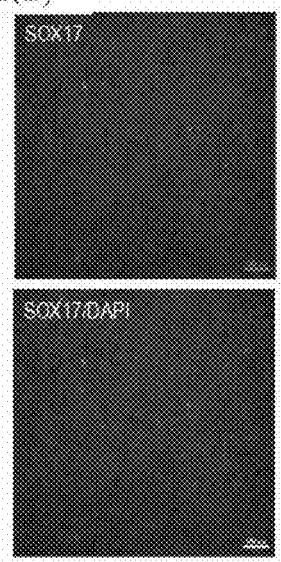
Fig.2(C)
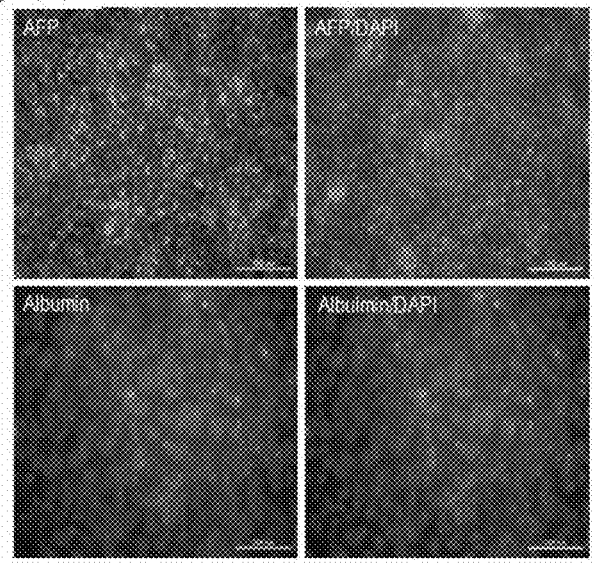

Fig.3(C)
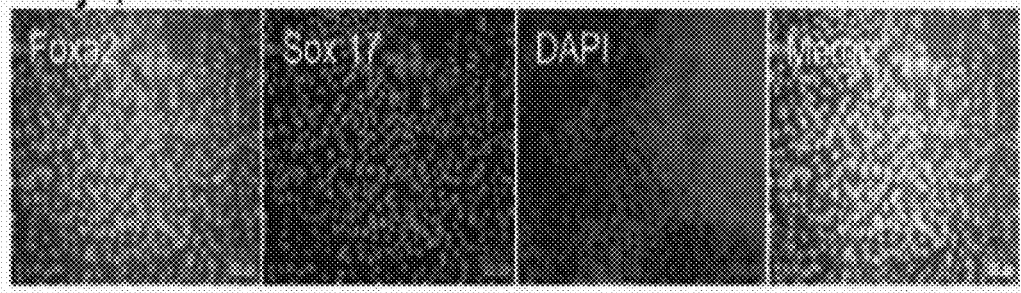
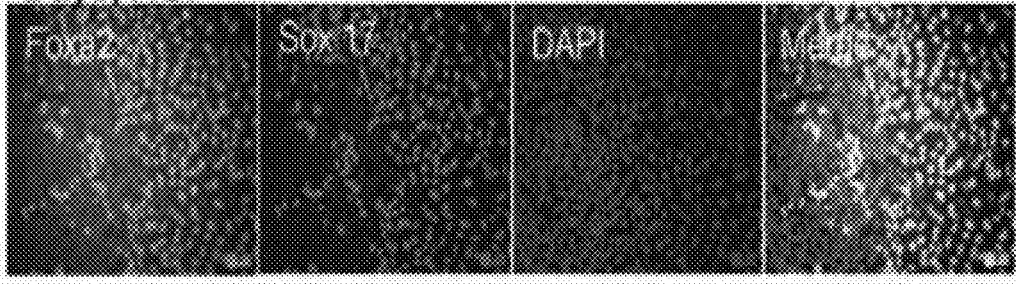

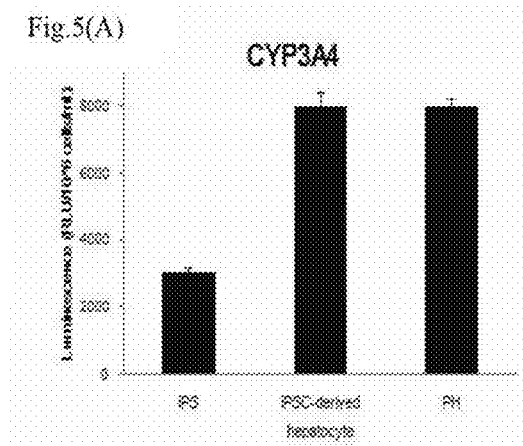
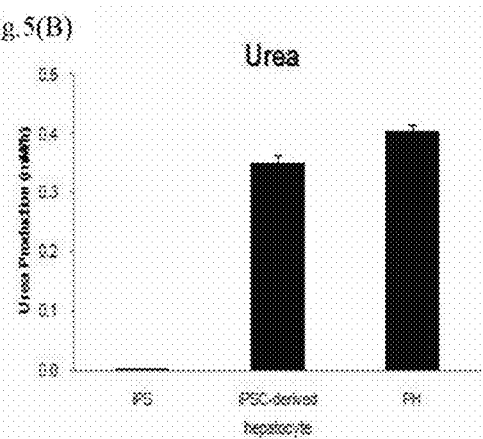
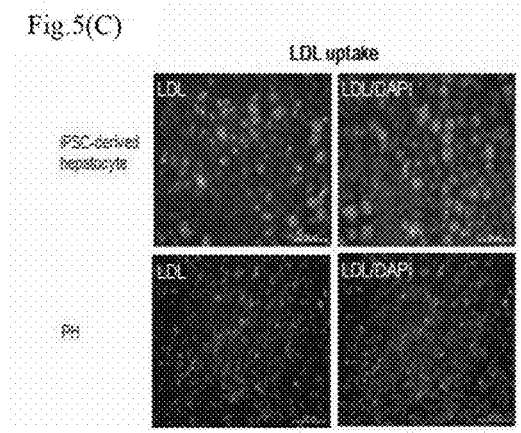
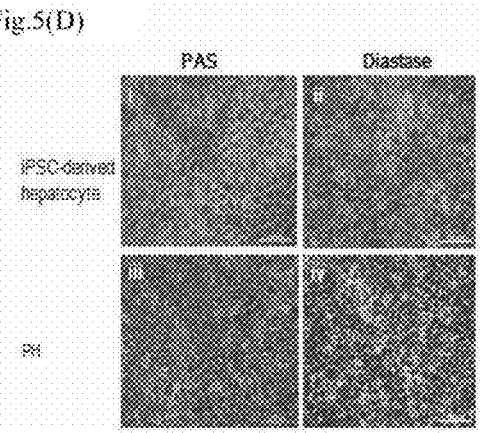

SEQUENCE LISTING

```
<160> NUMBER OF SEQ ID NOS: 20

<210> SEQ ID NO 1
<211> LENGTH: 18
<212> TYPE: DNA
<213> ORGANISM: Artificial sequence
<220> FEATURE:
<223> OTHER INFORMATION: forward primer

<400> SEQUENCE: 1
gcagccaaag tgaagagg                                                  18

<210> SEQ ID NO 2
<211> LENGTH: 18
<212> TYPE: DNA
<213> ORGANISM: Artificial sequence
<220> FEATURE:
<223> OTHER INFORMATION: reverse primer

<400> SEQUENCE: 2
tgttgctgcc tttgtttg                                                  18

<210> SEQ ID NO 3
<211> LENGTH: 20
<212> TYPE: DNA
<213> ORGANISM: Artificial sequence
<220> FEATURE:
<223> OTHER INFORMATION: forward primer

<400> SEQUENCE: 3
ggcacaatga agtgggtaac                                                20

<210> SEQ ID NO 4
<211> LENGTH: 18
<212> TYPE: DNA
<213> ORGANISM: Artificial sequence
<220> FEATURE:
<223> OTHER INFORMATION: reverse primer

<400> SEQUENCE: 4
aggcaatcaa caccaagg                                                  18
```

<210> SEQ ID NO 5
<211> LENGTH: 20
<212> TYPE: DNA
<213> ORGANISM: Artificial sequence
<220> FEATURE:
<223> OTHER INFORMATION: forward primer

<400> SEQUENCE: 5
ctacatcaac aaccttaggc                                          20

<210> SEQ ID NO 6
<211> LENGTH: 18
<212> TYPE: DNA
<213> ORGANISM: Artificial sequence
<220> FEATURE:
<223> OTHER INFORMATION: reverse primer

<400> SEQUENCE: 6
tccacatcct tcttgatg                                            18

<210> SEQ ID NO 7
<211> LENGTH: 20
<212> TYPE: DNA
<213> ORGANISM: Artificial sequence
<220> FEATURE:
<223> OTHER INFORMATION: forward primer

<400> SEQUENCE: 7
ttccctgtaa cctgtgagac                                          20

<210> SEQ ID NO 8
<211> LENGTH: 19
<212> TYPE: DNA
<213> ORGANISM: Artificial sequence
<220> FEATURE:
<223> OTHER INFORMATION: reverse primer

<400> SEQUENCE: 8
attcaagcac cgaaatctg                                           19

<210> SEQ ID NO 9
<211> LENGTH: 20
<212> TYPE: DNA
<213> ORGANISM: Artificial sequence
<220> FEATURE:
<223> OTHER INFORMATION: forward primer

<400> SEQUENCE: 9
ccaagtacat cccagctttc                                          20

<210> SEQ ID NO 10
<211> LENGTH: 18
<212> TYPE: DNA
<213> ORGANISM: Artificial sequence
<220> FEATURE:
<223> OTHER INFORMATION: reverse primer

<400> SEQUENCE: 10
ttggcatctg ggtcaaag                                            18

<210> SEQ ID NO 11
<211> LENGTH: 18
<212> TYPE: DNA
<213> ORGANISM: Artificial sequence
<220> FEATURE:
<223> OTHER INFORMATION: forward primer

<400> SEQUENCE: 11
ggaactacct gcatttgg                                             18

<210> SEQ ID NO 12
<211> LENGTH: 21
<212> TYPE: DNA
<213> ORGANISM: Artificial sequence
<220> FEATURE:
<223> OTHER INFORMATION: reverse primer

<400> SEQUENCE: 12
tctctgaagt cattgaagtc c                                         21

<210> SEQ ID NO 13
<211> LENGTH: 20
<212> TYPE: DNA
<213> ORGANISM: Artificial sequence
<220> FEATURE:
<223> OTHER INFORMATION: forward primer

<400> SEQUENCE: 13
actgtgtttg gaaacctgcc                                           20

<210> SEQ ID NO 14
<211> LENGTH: 20
<212> TYPE: DNA
<213> ORGANISM: Artificial sequence
<220> FEATURE:
<223> OTHER INFORMATION: reverse primer

<400> SEQUENCE: 14
gcagccactt gtcagaatga                                           20

<210> SEQ ID NO 15
<211> LENGTH: 22
<212> TYPE: DNA
<213> ORGANISM: Artificial sequence
<220> FEATURE:
<223> OTHER INFORMATION: forward primer

<400> SEQUENCE: 15
ccttacatat acacaccctt tg                                        22

<210> SEQ ID NO 16
<211> LENGTH: 23
<212> TYPE: DNA
<213> ORGANISM: Artificial sequence
<220> FEATURE:
<223> OTHER INFORMATION: reverse primer

<400> SEQUENCE: 16
ggttgaagaa gtcctcctaa gct                                       23

<210> SEQ ID NO 17
<211> LENGTH: 21
<212> TYPE: DNA
<213> ORGANISM: Artificial sequence
<220> FEATURE:
<223> OTHER INFORMATION: forward primer

<400> SEQUENCE: 17
ctgccaatcc tcttgagttc c                                         21

<210> SEQ ID NO 18

```
<211> LENGTH: 24
<212> TYPE: DNA
<213> ORGANISM: Artificial sequence
<220> FEATURE:
<223> OTHER INFORMATION: reverse primer

<400> SEQUENCE: 18
actcggtagc agaaagaata catc                                           24

<210> SEQ ID NO 19
<211> LENGTH: 18
<212> TYPE: DNA
<213> ORGANISM: Artificial sequence
<220> FEATURE:
<223> OTHER INFORMATION: forward primer

<400> SEQUENCE: 19
gagtccactg gcgtcttc                                                  18

<210> SEQ ID NO 20
<211> LENGTH: 21
<212> TYPE: DNA
<213> ORGANISM: Artificial sequence
<220> FEATURE:
<223> OTHER INFORMATION: reverse primer

<400> SEQUENCE: 20
gactgtggtc atgagtcctt c                                              21
```

METHODS FOR PRODUCING MATURE HEPATOCYTES

BACKGROUND OF THE INVENTION

Field of the Invention

The present invention relates to a process for generating hepatocyte cells derived from human induced pluripotent stem cells (iPSCs). In particular, the process can induce the differentiation of iPS cells into functional hepatocyte cells in less than 20 days, especially less than 15 days. The iPSC-derived hepatocyte cells have the similar gene expression profile to mature hepatocytes, and can be used in treatment of liver diseases.

Brief Discussion of the Related Art

Viral hepatitis or drugs often cause liver injury and cirrhosis. Liver transplantation is the only effective treatment for end-stage liver diseases; however, serious side effects of chronic immunosuppression and lack of suitable donor livers are major obstacles to liver transplantation. Reprogramming of mouse and human somatic cells to become induced pluripotent stem cells (iPSCs) has recently been achieved by viral transduction using four transcription factors (Takahashi K, et al. *Cell* 131:861-872, 2007). Unlike human embryonic stem (ES) cells, human iPSCs provide an alternative approach that avoids the controversies associated with the use of human embryos to obtain pluripotent ES cells. Although their gene expression pattern is not identical to human ES cells, human iPSCs are pluripotent and able to differentiate into most, if not all, cell types of the body. Therefore, human iPSC-derived somatic cells, such as hepatocytes, would be able to serve as an alternative source for liver transplantation, as well as help with toxicity screening during drug discovery.

During embryonic development, epiblast cells receive sequential developmental cues and undergo epithelial-to-mesenchymal transition to generate mesoderm or definitive endoderm. Several studies have successfully generated hepatocyte-like cells from human ES cells (Rambhatla L, et al. *Cell Transplant* 12:1-11, 2003; Cai J, et al. *HEPATOLOGY* 45:1229-1239, 2007; Hay D C, et al. *Cloning Stem Cells* 9:51-62, 2007; Touboul T, et al. *HEPATOLOGY* 51:1754-1765, 2010); and human iPSCs (Song Z, et al. *Cell Res* 19:1233-1242, 2009; Sullivan G J, et al. *HEPATOLOGY* 51:329-335, 2010; Ghodsizadeh A, et al. *Stem Cell Rev* 6:622-632, 2010; Si-Tayeb K, et al. *HEPATOLOGY* 51:297-305, 2010) in vitro.

However, most of previous studies have focused on how to develop an efficient differentiation protocol with which to generate functional hepatocyte-like cells. The conventional differentiation protocols require a period of at least 3 weeks (about 21 days or more) to generate functional hepatocyte-like cells. For the clinical usage of liver cell transplantation as an alternative option for treatment of liver diseases, it is needed to develop a rapid differentiation process to induce iPSCs into mature hepatocyte cells in less than 20 days (preferably less than 15 days).

Under the culture conditions for the generation of the hepatocyte-like cells, human ES cells or human iPSCs are first differentiated into definitive endoderm, followed by generation of mature hepatocytes that express stage- and tissue-specific genes (D'Amour K A, et al. *Nat Biotechnol* 23:1534-1541, 2005).

Hepatocyte growth factor (HGF) is essential for the development of liver. Previous studies demonstrated that HGF knockout mice fail to completely develop their liver architecture, with a loosened liver structure and dissociation of the parenchymal cells in the mouse model (Schmidt C, et al. *Nature* 373:699-702, 1995). HGF and its receptor c-MET also exert several important functions that are associated with cell proliferation, survival, motility, invasion, and morphogenesis (Liu X, Newton R C, Scherle P A. *Trends Mol Med* 16:37-45, 2010). In addition to its pathophysiological functions, HGF has been shown to induce scattering of epithelial cells by up-regulating expression of Snail, which is a transcription repressor that directly targets E-cadherin. However, HGF-associated molecular mechanisms during embryonic development are still poorly understood. In our previously published study, we successfully generated hepatocyte-like cells from mesenchymal stem cells in vitro by a two-step protocol involving HGF and oncostatin M (Lee K D, et al., 2004, *Hepatology* 40:1275-1284).

SUMMARY OF THE INVENTION

In the present invention, we describe an efficient three-step protocol that is capable to rapidly induce the differentiation of induced pluripotent stem cells (iPSCs) into hepatocyte cells in less than 20 days. In the method of the present invention, definitive endoderm formation is significantly improves during the endodermal induction step involving HGF and activin A signaling; subsequently, functional hepatocyte cells can be generated in vitro.

Thus, in one aspect of the invention, it is provided a method for rapid generation of mature hepatocytes from human induced pluripotent stem cells. The method of the invention is characterized by inducing the hepatic endoderm formation of iPSCs in a culture condition comprising high level of activin A, wingless-type MMTV integration site family, member 3A (Wnt3a), and hepatocyte growth factor (HGF); and inducing the hepatocyte differentiation in a hepatic commitment medium.

In one embodiment, the method comprises steps of: (1) preinduction, culturing human induced pluripotent stem cells (iPSCs) in MEF-conditioned medium (Dulbecco's modified Eagle medium [DMEM]/F12 supplemented with 20% knockout serum replacement, 10 ng/mL basic fibroblast growth factor, 1 mM L-glutamine, 100 µM nonessential amino acids, 100 µM 2-mercaptoethanol, 50 U/mL penicillin, and 50 mg/mL streptomycin) to 70% confluence; (2) endodermal induction, replacing the MEF-conditioned medium with culture medium containing 100 ng/mL activin A, 50 ng/mL Wnt3a, and 10 ng/mL HGF, and culturing the cells for 3-5 days; (3) hepatic lineage commitment, replacing the culture medium with hepatic commitment medium (knockout [KO]/DMEM containing 20% knockout serum replacement, 1 mM L-glutamine, 1% nonessential amino acids, 0.1 mM 2-mercaptoethanol, and 1% dimethyl sulfoxide), and culturing the cells for 4-6 days; and (4) maturation, culturing cells in IMDM containing 20 ng/mL oncostatin M, 0.5 µM dexamethasone, and 50 mg/mL ITS (insulin, transferrin, selenous acid) premix for 5-7 days to obtain mature hepatocyte cells.

In other embodiments, the human iPSCs are cultured in feeder-free conditions before the hepatogenic differentiation to maintain their pluripotent properties.

The iPSC-derived hepatocyte cells obtained by the method have the similar gene expression profile to mature human liver cells. The iPSC-derived hepatocyte cells also exhibit functions of urea production, LDL uptake and glycogen storage.

In another aspect of the invention, it is provided a composition comprising a culture of iPSC-derived hepatocyte cell obtained by the method of the invention.

According to our experimental results demonstrating that the carbon tetrachloride ($CCl_4$)-induced lethal fulminant hepatic failure in nonobese diabetic severe combined immunodeficient (NOD-SCID) mice can be rescued by intrasplenic transplantation of the iPSC derived hepatocytes, it is possible to use the iPSC-derived hepatocyte cells of present invention in treating or preventing liver injury caused by acute or chronic liver diseases.

In a further aspect, the present invention relates to a method for treating or preventing liver injury caused by acute or chronic liver diseases, which comprises administration of a composition comprising the iPSC-derived hepatocyte cell culture of present invention to a subject needed thereof. In one preferable embodiment, the method involves transplantation of iPSC-derived hepatocyte cells of present invention into a subject having liver disease.

Other features or advantages of the present invention will be apparent from the following drawings and detailed description of several embodiments, and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2(A) depicts the images showing the sequential morphological change from human iPSCs to hepatocyte-like cells. (Panel i) Morphology at the preinduction stage of human iPS cells; Panel ii shows the morphological changes that occur to give a spiky shape after culture in endodermal induction medium. (Panel iii) At day 7 after hepatic lineage commitment medium induction, the cell morphology has become polygonal in shape. (Panel iv) The morphology of the mature hepatocyte-like cells. FIG. 2(B) depicts the result of immunocytochemistry showing that the expression of the definitive endoderm marker SOX17 at day 4, and FIG. 2(C) shows that the cells are positive for AFP and albumin at day 12 after the start of the differentiation procedure. Scale bars, 100 μm. (Original magnification, ×100). DAPI, 4',6-diamidino-2-phenylindole.

FIG. 3(C) depicts the result of immunocytochemistry showing the expression of the colocalized definitive endoderm markers SOX17 and Foxa2 at day 5; the upper panel shows endodermal induction medium with HGF and the lower panel shows endodermal induction medium without HGF. (Original magnification, ×100).

FIG. 5(A) depicts functional analysis of the hepatocyte cells derived from iPSCs, showing that the human iPSC-derived hepatocytes exhibited cytochrome P450 isozyme activity similar to primary human hepatocytes (n=3), after 12 days induction. FIG. 5(B) shows that human iPSC-derived hepatocytes also secreted urea after 12 days induction. FIG. 5(C) depicts the result of immunofluorescence staining for LDL uptake in iPSC-derived hepatocytes. FIG. 5(D) depicts the result of PAS staining for examining glycogen storage (panel i), which begins to show glycogen storage at differentiation day 12. (Panel ii) shows that glycogen stored in hepatic cells can be digested by diastase treatment and is then present as negative PAS staining. The primary human hepatocytes were used as a positive control (Panels iii and iv). (Original magnification, ×100).

DETAILED DESCRIPTION OF THE PREFERRED EMBODIMENTS

Figure 1:
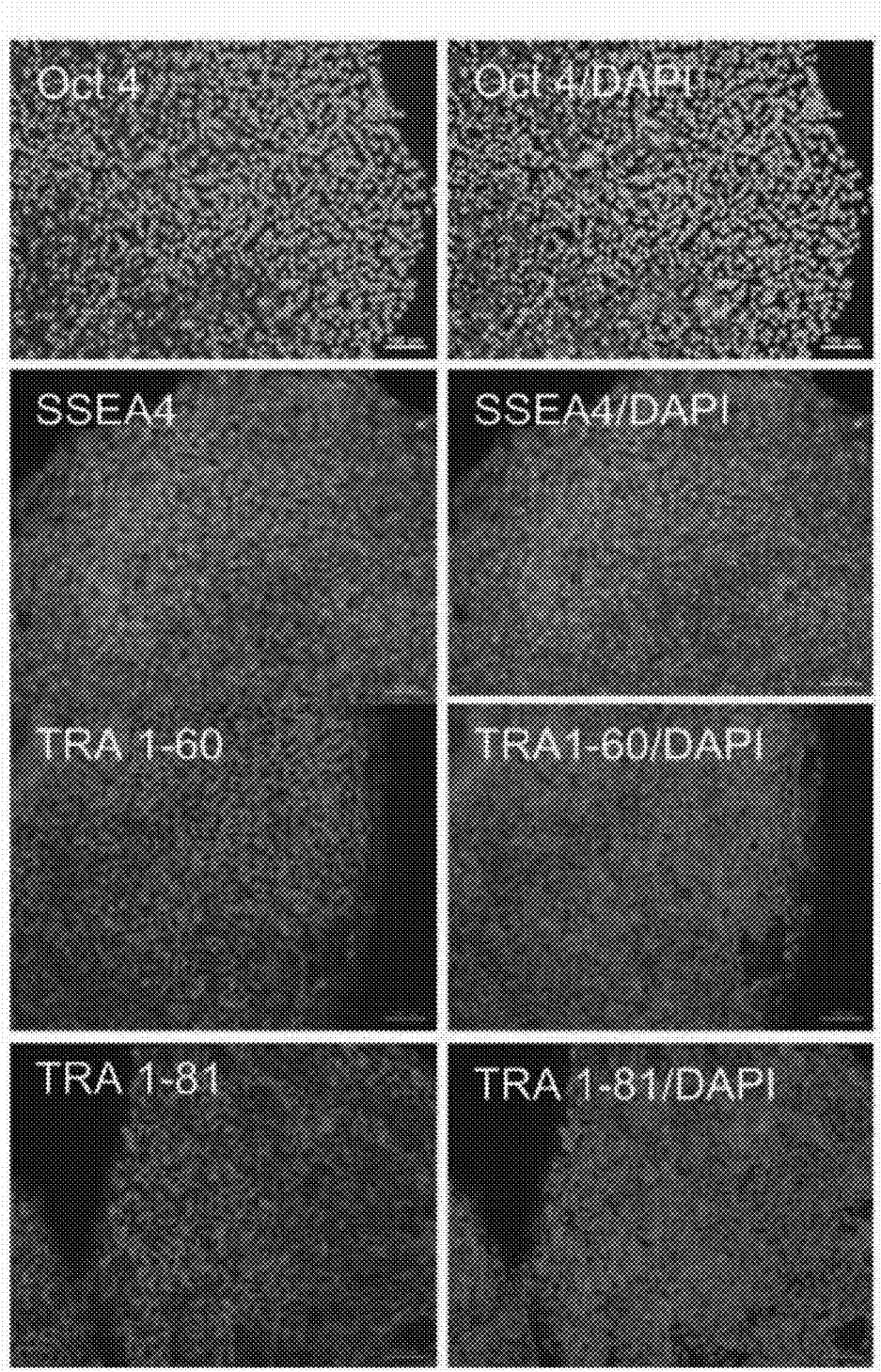
FIG. 1 depicts analysis result of human iPSCs cultured on Matrigel with MEF-conditioned medium, showing the expression of the stemness markers, Oct4, SSEA4, TRA-1-60, and TRA-1-81, when cultured on Matrigel-coated dishes with MEF-conditioned medium. Scale bars, 100 μm. (Original magnification, ×100). DAPI, 4',6-diamidino-2-phenylindole.

A main character of the in vitro differentiation process proved in this invention is using high level of activin, Wnt signaling, and HGF in the induction of definitive endoderm formation, which benefits the further differentiation of human iPSCs into hepatic lineage and the maturation to functional hepatocyte cells.

For better understanding the present invention, the following terms and phrases shall have the meanings set forth below. Unless defined otherwise, all technical and scientific terms used herein have the same meaning as commonly understood to one of ordinary skill in the art.

As used herein, "induced pluripotent stem cells (iPSCs)" refers to a type of pluripotent stem cell artificially derived by transfection of certin stem cell-associated genes into a non-pluripotent cell, typically an adult somatic cell such as skin cell, to induce a "forced" expression of the genes. Transfection is typically achieved through viral vectors, such as retroviruses. Induced Pluripotent Stem Cells are identical to embryonic stem (ES) cells in the respect of potency and differentiability into various types of functional cells.

As used herein, "rapid differentiation" of induced pluripotent stem cells (iPSCs) into mature hepatocyte cells means that iPS cells can be induced to differentiate into functional hepatocyte cells in a short period (less than 20 days, preferably less than 15 days) using the process of the invention, when compared to conventional differentiation processes needing at least 3 weeks (about 21 days or more) to generate functional hepatocyte-like cells. In one embodiment of present invention, it is provided an in vitro differentiation process to generate functional hepatocyte cells from human iPSCs requiring only 12 days.

According to the in vitro differentiation process of the invention, "mature hepatocyte cells" or "mature hepatocyte cells" derived from human iPSCs refers to the differentiated hepatocyte cells having the similar gene expression profile to primary human liver cells, and exhibiting functions of urea production and glycogen storage.

The preferred embodiments described below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EMBODIMENTS

Embodiment 1

In Vitro Differentiation of Human iPSCs into Mature Hepatocyte Cells

Materials and Methods

Cell and Cell Culture.

Human ES cell line H9 (National Institutes of Health Code: GE09) and human iPSC line CFB46 were maintained on mitomycin-C (Sigma-Aldrich, St Louis, Mo.) inactivated mouse embryonic fibroblast (MEF) feeder layer in ES cell medium (Dulbecco's modified Eagle medium [DMEM]/F12 supplemented with 20% knockout serum replacement, 10 ng/mL basic fibroblast growth factor, 1 mM L-glutamine, 100 μM nonessential amino acids, 100 μM 2-mercaptoethanol, 50 U/mL penicillin, and 50 mg/mL streptomycin [Invitrogen, Carlsbad, Calif.]). Before differentiation, the cells were cultured on Matrigel-coated tissue culture dishes using MEF-conditioned medium.

In Vitro Differentiation of Human iPSCs into Hepatocyte Cells.

The in vitro differentiation protocol was similar to our previously reported study and that of Hay et al. In brief, when human iPSCs had attained a confluence of 70%, the MEF-conditioned medium was replaced with Roswell Park Memorial Institute/B27 with 100 ng/mL activin A (Pepro-Tech, London, UK), 50 ng/mL Wnt3a, and 10 ng/mL HGF (R&D Systems) for 3 days of endodermal induction. During the next step, the culture medium was replaced with hepatic commitment medium (knockout [KO]/DMEM containing 20% knockout serum replacement, 1 mM L-glutamine, 1% nonessential amino acids, 0.1 mM 2-mercaptoethanol, and 1% dimethyl sulfoxide). Finally, during the maturation step, the cells were culturing in Iscove's modified Dulbecco's medium (IMDM) supplemented with 20 ng/mL oncostatin M (Invitrogen), 0.5 μM dexamethasone, and 50 mg/mL ITS (Insulin, Transferrin, Selenous acid) premix (BD Biosciences, San Jose, Calif.).

The medium contents and cultivating time used in each step of the differentiation protocol is summarized in Table 1.

TABLE 1

Hepatogenic Differentiation Condition

| | Induction period | Medium contents |
| --- | --- | --- |
| Preinduction | Day −4 to Day 0 | CM (MEF-conditioned medium) |
| Endodermal induction | Day 1 to Day 3 | RPMI/B27, activin A (100 ng/mL), Wnt 3a (50 ng/mL), HGF (10 ng/mL) |
| Hepatic lineage commitment | Day 4 to Day 7 | KO/DMEM, L-glutamine (1 mM), nonessential amino acids (1%), 2-Mercaptoethanol (0.1 mM), dimethyl sulfoxide (1%) |
| Maturation | Day 8 to Day 12 | IMDM, oncostatin M (20 ng/mL), dexamethasone (0.5 μM), ITS premix (50 mg/mL) |

Immunofluorescence.

Human ES and iPS cells were fixed in 4% paraformaldehyde/PBS for 20 minutes and then the cells were permeabilized with 0.1% Triton X-100/PBS for 10 minutes at room temperature. Slides or dishes were incubated with blocking solution (4% normal goat serum/PBS) for 30 minutes. The cells were subsequently incubated overnight at 4° C. with primary antibodies. This was followed by incubation with fluorescein secondary antibody for 45 minutes. Between incubations, the samples were washed with Rinse Buffer (0.05% Tween20 in PBS). Fluorescence images were visualized and captured using an Olympus AX80 microscope.

Histopatholoy and Immunohistochemical Staining.

Organs were fixed in formalin and prepared in paraffin-embedded blocks for sectioning at 4-micrometer thickness. The sections were deparafinized in xylene and rehydrated in graded series of ethanol. Epitope retrieval was performed by microwave boiling the deparaffinized sections in 10 mM sodium citrate, 0.05% tween 20, pH 6.0 for 20 minutes. The sections were then incubated with primary HepPar1 antibody (clone OCH1E, IR62461, Dako, Carpinteria, Calif.) and anti-human albumin antibody (2.5 μg/mL, Abcam Inc., Cambridge, Mass., USA) at the room temperature for 40 minutes, followed by staining with goat antibodies against rabbit IgG (Dako), or goat anti-mouse IgG antibody (Dako) for another 40-60 minutes.

RNA Isolation and Quantitative Real-Time RT-PCR.

RNA was extracted using an RNeasy kit (Qiagen, Chatsworth, Calif.) and treated with RNase-free DNase according to manufacturer's instructions. Then, 1 μg RNA was reverse transcribed to cDNA using Moloney murine leukemia virus reverse transcriptase (M-MLV Reverse Transcriptase, Promega. Madison, Wis.). For the reverse-transcription polymerase chain reaction (RT-PCR), the following conditions were used: 94° C. for 40 seconds, 56° C. for 50 seconds, 72° C. for 60 seconds for 30 cycles, after an initial denaturation at 94° C. for 5 minutes. The primers used are listed in Table 2. Quantitative real-time RT-PCR (Q-PCR) was performed using the StepOnePlus™ Real-Time PCR System (Applied Biosystems, Foster City, Calif.), and glyceraldehyde 3-phosphate dehydrogenase (GAPDH) was used to quantify the messenger RNA levels. The genes expression levels were normalized against primary human hepatocytes.

Periodic Acid-Schiff (PAS) Staining for Glycogen and LDL Uptake Assays.

Differentiated cells were fixed in 4% formaldehyde for 20 minutes and then permeabilized with 0.1% Triton X-100 for 10 minutes. The cells were next either treated or not treated with Diastase (Sigma-Aldrich) for 1 hour, 37° C. The samples were then oxidized in 1% periodic acid for 5 minutes, rinsed three times in de-ionized (d) $H_2O$, treated with Schiff's reagent (Sigma-Aldrich) for 20 minutes in dark, and rinsed in $dH_2O$ for 5 minutes. Finally, they were visualized under light microscope. LDL uptake by cells was assessed by LDL Uptake Cell-Based Assay kit (Cayman, Ann Arbor, Mi) according to manufacturer's instructions.

Cytochrome P450 Activity.

CYP3A4 activity was measured using a P450-Glo Assays kit (Promega) according to the manufacturer's instructions. In brief, the cells were washed with phosphate-buffered saline, then this was replace with fresh medium containing luminogenic CYP3A4 substrate luciferin-PFBE for 4 hours incubation at 37° C. To determine CYP P450 enzyme activity, 50 µL of medium was transferred and 50 µL Luciferin Detection Reagent added to initiate a luminescent reaction for 20 minutes. The luminescence of the mixture was then read using an Infinite M1000 (TECAN Group Ltd.) luminometer. Cytochrome activity was stated as relative light units (RLU)/$10^6$ cells/mL.

Urea Production.

Urea production by the differentiated cells was determined by Urea Assay Kit (BioVision, Inc., USA) according to the manufacturer's instructions. Briefly, 25 µL of culture medium was directly added into 96-well plates and incubated with 50 µL of Assay Buffer for 60 minutes at 37° C. while protected from light. The amount of urea present was measured at O.D. 570 nm using a micro plate reader.

Hepatic Gene Expression.

The primer sequences used for reverse-transcription polymerase chain reaction are listed in Table 2.

TABLE 2

Primers Used for Reverse-Transcription Polymerase Chain Reaction

| Primer | Sequence | Product |
|---|---|---|
| AFP | F: GCA GCC AAA GTG AAG AGG<br>R: TGT TGC TGC CTT TGT TTG | 284 bp |
| Albumin | F: GGC ACA ATG AAG TGG GTA AC<br>R: AGG CAA TCA ACA CCA AGG | 157 bp |
| CK-18 | F: CTA CAT CAA CAA CCT TAG GC<br>R: TCC ACA TCC TTC TTG ATG | 177 bp |
| G-6P | F: TTC CCT GTA ACC TGT GAG AC<br>R: ATT CAA GCA CCG AAA TCT G | 144 bp |
| HNF-4 | F: CCA AGT ACA TCC CAG CTT TC<br>R: TTG GCA TCT GGG TCA AAG | 295 bp |
| TDO2 | F: GGA ACT ACC TGC ATT TGG<br>R: TCT CTG AAG TCA TTG AAG TCC | 307 bp |
| TAT | F: ACT GTG TTT GGA AAC CTG CC<br>R: GCA GCC ACT TGT CAG AAT GA | 188 bp |
| CYP3A4 | F: CCT TAC ATA TAC ACA CCC TTT G<br>R: GGT TGA AGA AGT CCT CCT AAG CT | 169 bp |
| CYP7A1 | F: CTG CCA ATC CTC TTG AGT TCC<br>R: ACT CGG TAG CAG AAA GAA TAC ATC | 387 bp |
| GAPDH | F: GAG TCC ACT GGC GTC TTC<br>R: GAC TGT GGT CAT GAG TCC TTC | 246 bp |

Abbreviations: AFP, alpha-fetoprotein; CK-18, cytokeratin 18; G-6P, glucose-6-phosphatase; HNF-4, hepatocyte nuclear factor-4; TDO2, tryptophan 2,3-dioxygenase; TAT, tyrosine-aminotransferase; CYP3A4, cytochrome P450 3A4; CYP7A1, cytochrome P450 7A1; GAPDH, glyceraldehyde 3-phosphate dehydrogenase.

Microarray Gene Expression Analysis.

RNA was isolated from human iPSCs and human iPSC-derived hepatocyte-like cells, using the RNeasy kit (Qiagen). Complementary DNA synthesis, fragmentation, hybridization, washing, staining, and scanning were performed at the National Research Progress for Genomic Medicine Microarray and Gene Expression Analysis Core Facility, National Yang-Ming University VYM Genome Research Center, Taiwan. To provide a visual impression of how the various sample groups are related, principal component analysis (PCA) was performed using the Partek Genomics Suite program (Partek Inc., St. Louis, Mo.). Array data of control iPSCs and differentiated hepatocyte-like cells were downloaded from the GEO database (accession number GSE14897).

Results

Feeder-Free Human ES Cell Culture System and MEF-Conditioned Medium Maintain Human iPSCs in an Undifferentiated State.

Human iPSC and ES cell colonies were plated onto a MEF feeder layer for several months with weekly passaging. Before hepatogenic differentiation, cells were passaged using Matrigel-coated feeder-free culture conditions. On growing from day −4 to day 0, human iPSC and ES cell colonies were able to reach 70% confluence, and the cells showed positive expression of human ES cell surface markers, including octamer-binding transcription factor 4 (Oct-4), also known as POU5F1, stage-specific embryonic antigen 4 (SSEA-4), or the tumor rejection antigens Tra 1-60 and Tra 1-81 (FIG. 1). These results demonstrate that the human iPSCs exhibit pluripotent properties before hepatogenic differentiation.

Directed Hepatogenic Differentiation from Human iPSCs In Vitro.

It is imperative to ensure the differentiation abilities of the human iPSCs prior to therapeutic application. Here, we developed a three-step protocol by modifying the culture condition described by Hay et al., and Kuo et al., in order to bring about the rapid generation of hepatocyte-like cells from human iPSCs.

In this protocol, the human iPSCs were allowed to reach approximately 70% confluence in feeder cell-free culture system over 4 days, and this was followed by treatment with endodermal induction medium on day 0 (FIG. 2(A), panel i) in the presence of activin A, Wnt3a, and HGF. This produced a human iPSC morphology with a spiky shape due to the loss of ES cell structure that occurred after dissociation from cell-cell contact (FIG. 2(A), panel ii). Immunostaining revealed that most of the cells were positive for the definitive endoderm marker Sox17 (sex-determining region Y box 17;

FIG. 2(B)), indicating that the human iPSCs efficiently differentiated into definitive endoderm during the endodermal induction step.

Following the endodermal induction step, cells were treated with the hepatic commitment medium for 3 days; this changed the cell morphology from a spiky shape to a polygonal shape that had tight cell-cell contact (FIG. 2(A), panel iii). Finally, the medium was changed to maturation medium, which resulted in the human iPSC morphology changing into a cuboidal shape (FIG. 2(A), panel iv). Immunostaining of these cells confirmed that these hepatocyte-like cells were positive for alpha-fetoprotein (AFP) and albumin (ALB) (FIG. 2(C)).

Highly Efficient Endoderm Formation Requires Hepatocyte Growth Factor.

Figure 3A:
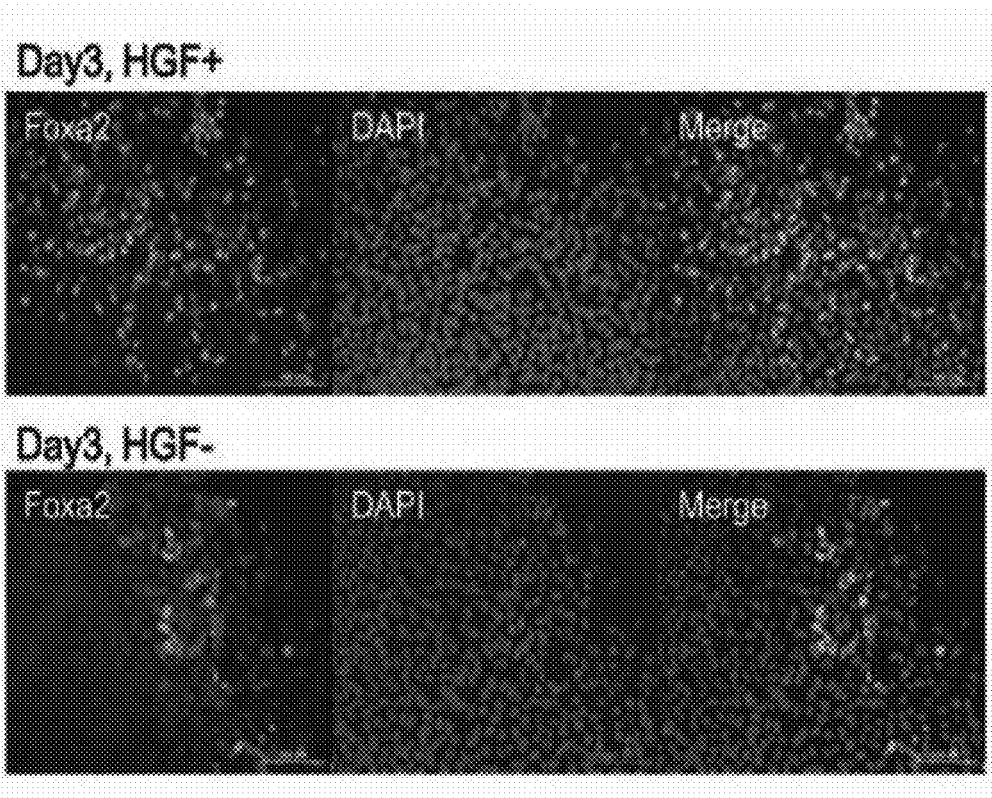
FIG. 3(A) depicts the immunocytochemical analysis of cells treated with endodermal induction medium with HGF or without HGF shows efficient production of the endoderm marker Foxa2 only in medium with HGF.
Figure 3B:
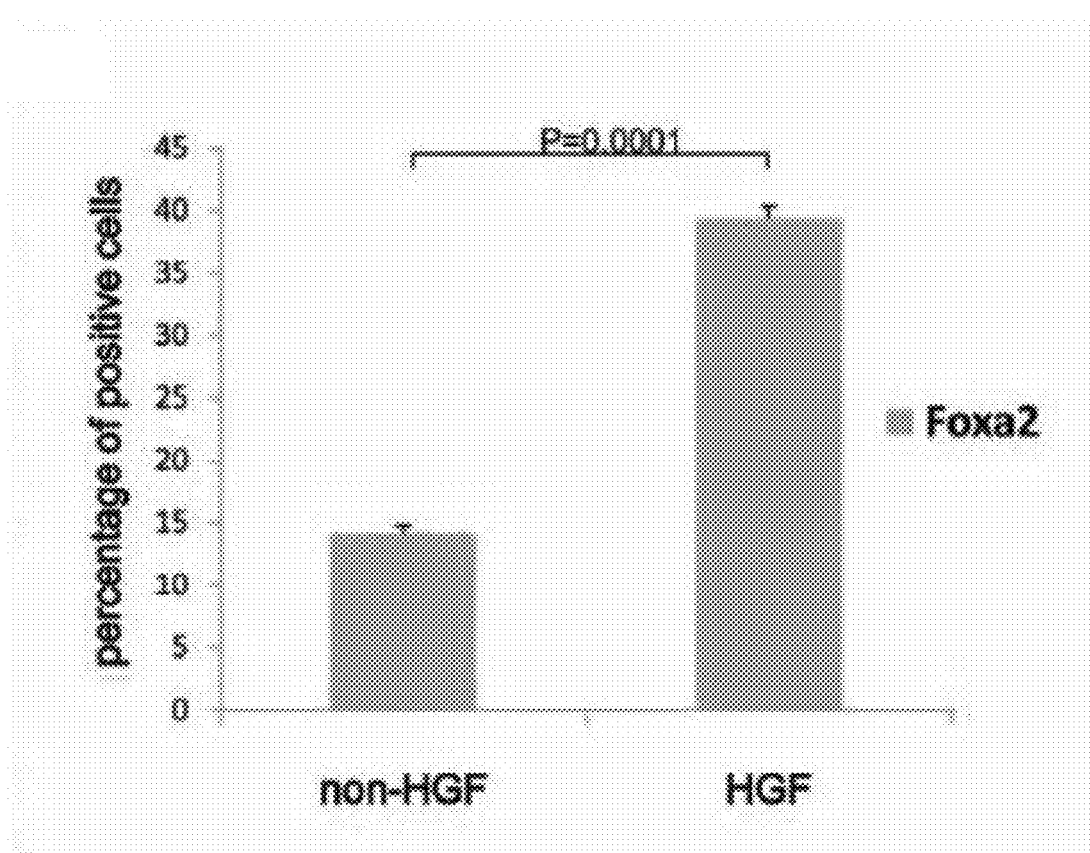
FIG. 3(B) and FIG. 3(D) shows quantitative analysis to confirm that there was a significant change between the cells grown in HGF+ and HGF− medium. Scale bars, 100 μm. (t test, n=3). DAPI, 4',6-diamidino-2-phenylindole.

HGF has multiple effects on target cells in culture and has been demonstrated to be involved in liver development. In our endodermal induction step, we were interested in how HGF acted synergistically with activin A and Wnt3a to accelerate definitive endoderm formation. To confirm this process, human iPSCs were induced in endodermal induction medium with or without HGF for 3 days. Consistent with definitive endoderm marker Sox17 expression, we observed that fork head box a2 (Foxa2), which is another endodermal marker, could be detected after the endodermal induction step (FIG. 3(A)). Moreover, differentiation into Foxa2$^+$ cells was detected in 39.35%±0.98% of iPSCs treated with HGF, compared to 14.18%+0.54% of iPSCs that did not have HGF treatment during the endodermal induction step (FIG. 3(B)). Compared with cells cultured in media without HGF, we found that the presence of HGF may have a synergistic effect with activin A and Wnt3a and is able to efficiently drive iPSCs toward a definitive commitment to endoderm formation.

Figure 3D:
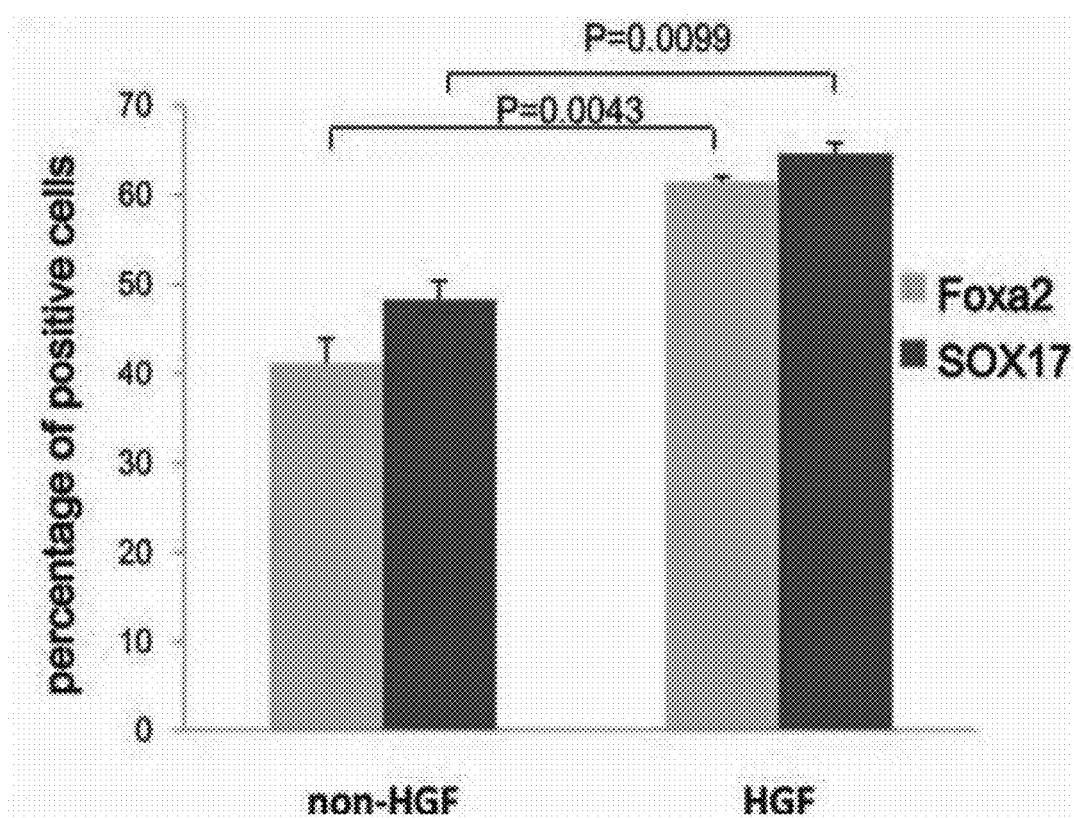

To further investigate whether HGF treatment results in increased formation of hepatic lineage cells, we examined the expression of Sox17 and Foxa2 expression at day 5. The results showed that Sox17 and Foxa2 coexisted during the hepatic commitment step (FIG. 3(C)). Coincident with the endodermal induction step, there was only 41% Foxa2$^+$ and 48% Sox17$^+$ cells in the group without HGF, but this increased to 61% Foxa2$^+$ and 64% Sox17$^+$ cells in the HGF-treated group (FIG. 3(C, D)). These results suggest that HGF plays an important role in early hepatic lineage formation.

Gene Expression Profile of the iPSC-Derived Hepatocyte-Like Cells.

Figure 4:
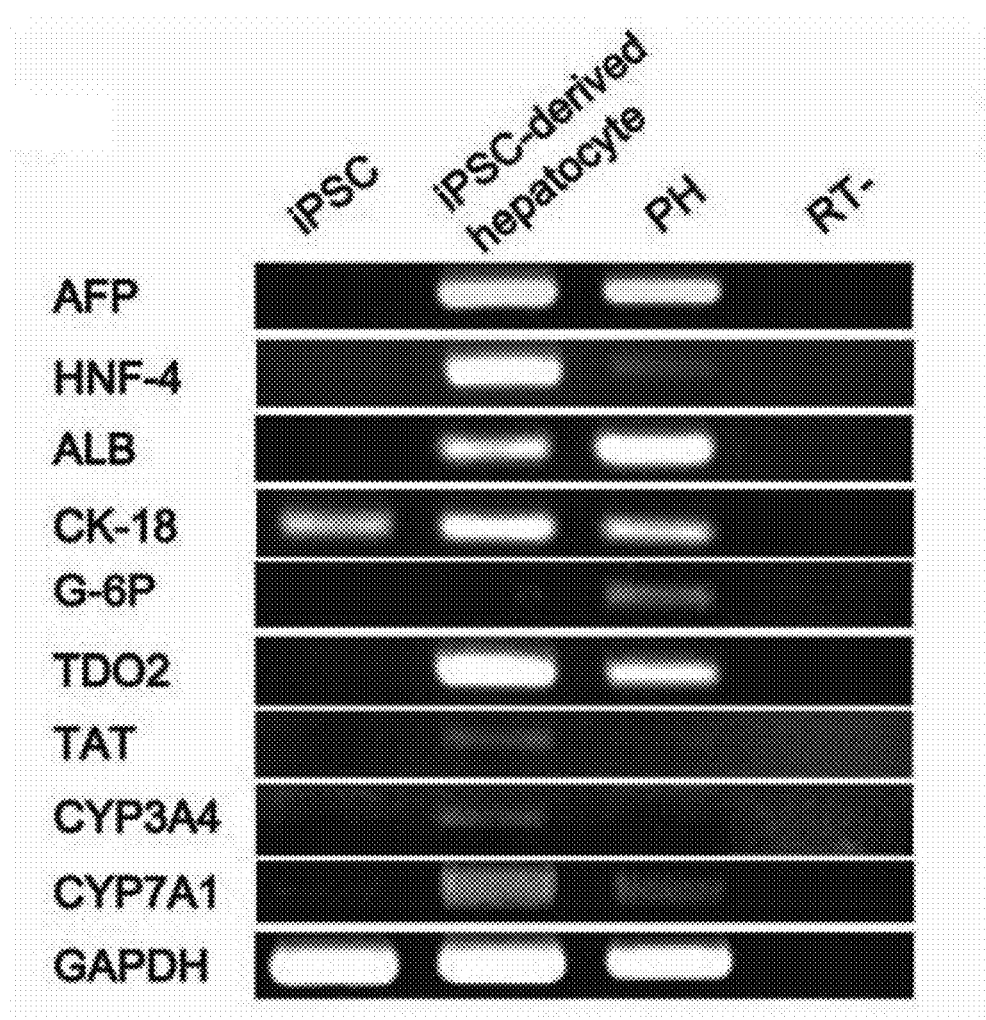
FIG. 4(A) depicts a diagram of reverse transcription polymerase chain reaction (RT-PCR) gene expression of human iPSCs and iPSC-derived hepatocyte cells for the hepatocyte markers alpha-fetoprotein (AFP), hepatocyte nuclear factor-4 (HNF-4), albumin (ALB), cytokeratin 18 (CK-18), glucose-6-phosphatase (G-6P), tryptophan 2,3-dioxygenase (TDO2), tyrosine aminotransferase (TAT), cytochrome P450 3A4 (CYP3A4), and cytochrome P450 7A1 (CYP7A1). Gene expressions were normalized to glyceraldehyde 3-phosphate dehydrogenase (GAPDH).
FIG. 4(B) shows quantitative PCR analysis of the hepatic markers AFP, ALB, CK-18, HNF4a, transthyretin (TTR), TAT, TDO2, dipeptidyl peptidase 4 (DPP4), and low-density lipoprotein receptor (LDLR). Gene expression levels were normalized against primary human hepatocytes.
FIG. 4(C) is the multidimensional scaling plot showing the discrimination ability of the molecular signatures of the cell groups. Each spot represents a single array sample. Each cell group exhibited a significant and distinct global gene expression profile (n=3). iHCFB46, iPSC-derived hepatocyte cells in our group; iPSC-CFB46, human iPS cells from the Kuo group; iH-T, iPSC-derived hepatocyte cells from the Si-Tayeb group; iPSC-T, human iPS cells from the Si-Tayeb group; PH, primary human hepatocyte cells.
Figure 4B:
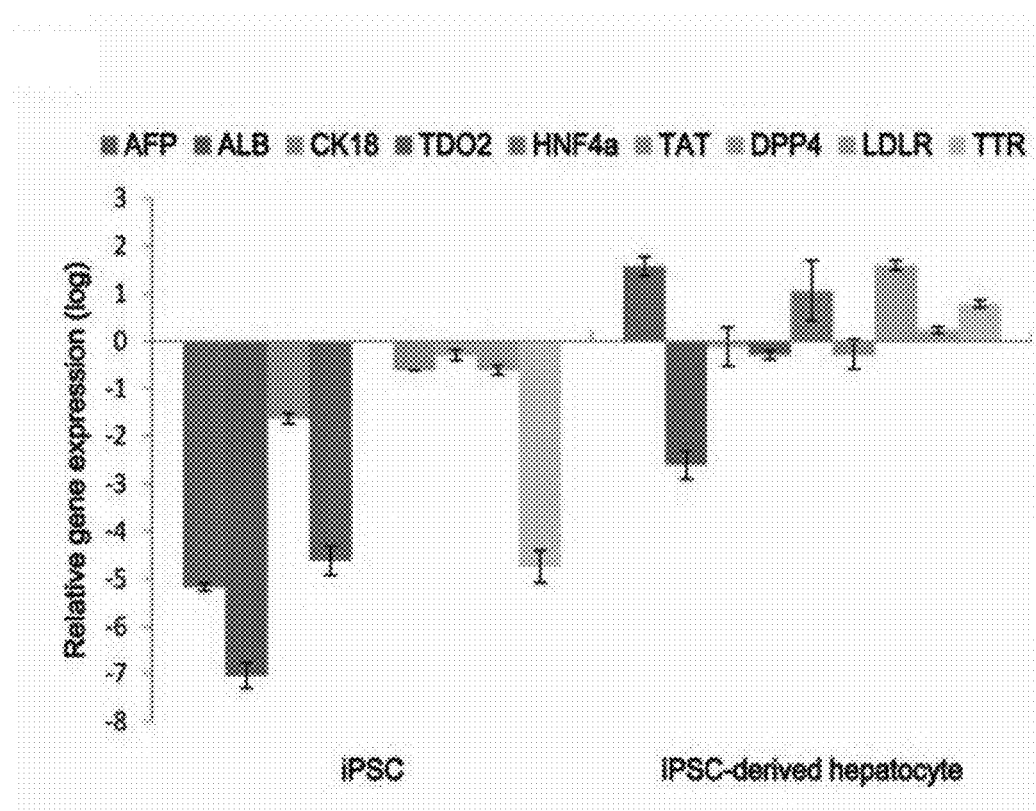

To determine whether iPSC derived hepatocytes in our differentiation system displayed mature characteristics of a hepatic lineage, we examined the gene expression patterns of various early hepatic marker genes, namely hepatocyte nuclear factor 4 (HNF-4), albumin, cytokeratin 18 (CK-18), glucose 6-phosphate (G-6P), cytochrome P450 3A4 (CYP3A4), and cytochrome P450 7A1 (CYP7A1) by reverse transcription polymerase chain reaction (RT-PCR) (FIG. 4(A)). As seen, all of these genes were expressed in iPSC-derived hepatocyte cells. To determine the quantitative expression levels of the hepatic markers in iPSCs before and after induction, we examined the gene expression patterns by quantitative PCR and normalized the results against primary human hepatocytes. The results reveal that the expression levels of the hepatic genes AFP, TDO2, and transthyretin (TTR) were significantly higher in the iPSC-derived hepatocyte cells than in the primary human hepatocytes. Furthermore, if we compared iPSCs with iPSC-derived hepatocyte cells, it was found that ALB, cytokeratin 18 (CK-18), HNF-4A, tyrosine aminotransferase (TAT), and low-density lipoprotein receptor (LDLR) are more highly expressed in the iPSC-derived hepatocyte cells (FIG. 4(B)).

Figure 4C:
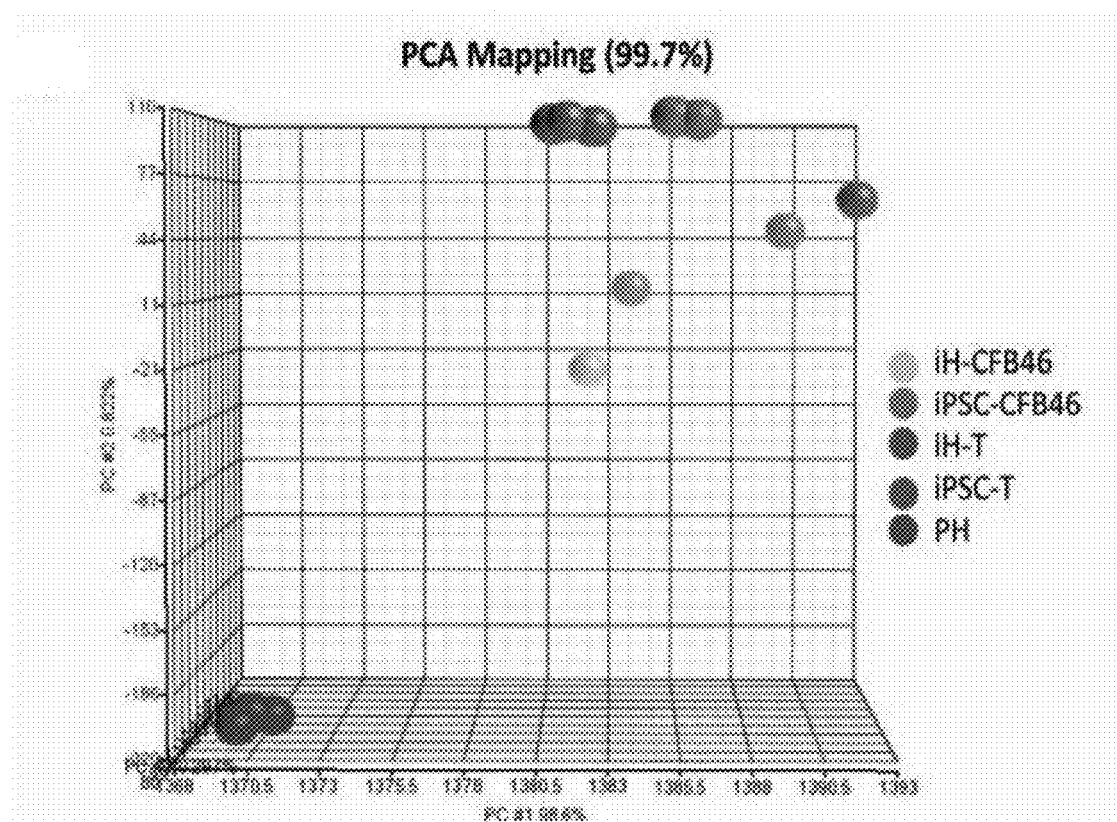

Gene expression microarray analysis of the differentiated cells (orange spots, iH-CFB46, FIG. 4(C)) compared to the iPSC-derived hepatocyte cells of the Si-Tayeb group (purple spots, iH, FIG. 4(C)) showed that the iPSC-derived hepatocyte cells were different from the original iPSCs (green and red spots iPSC and CFB46, respectively, FIG. 4(C)) and were closer to primary hepatocyte cells (blue spots, PH, FIG. 4(C)), with the differentiated cells being closer to primary hepatocytes.

Functional Characterization of the Human iPSCDerived Hepatocyte Cells.

To assess the functional status of the human iPSC-derived hepatocyte like cells, we determined their metabolic capacity. The cytochrome P450 enzyme isoform, cytochrome P450 3A4, is one of the most important enzymes involved in the metabolism of xenobiotics in the liver. Our results demonstrated that the differentiated cells exhibited CYP3A4 activity similar to that found in primary human hepatocytes and that the expression level of the enzyme was remarkably higher than human iPSCs (FIG. 5(A)). Secretion of urea by the differentiated cells was also analyzed. Urea production was detectable on day 12 (FIG. 5(B)). In addition, iPSC derived hepatocytes were competent for LDL uptake (FIG. 5(C)).

To further characterize the glycogen storage function of iPSC-derived hepatocyte-like cells, the presence of stored glycogen was determined by periodic acid-Schiff (PAS) staining. Glycogen was stained magenta and could be seen in the differentiated cells (day 12; FIG. 5(D), panel i). Diastase digestion was subsequently performed, which confirmed that positive staining was due to the presence of glycogen (FIG. 5(D), panel ii). Primary human hepatocytes were used as a positive control (FIG. 5(D), panels iii and iv).

Embodiment 2 iPSC-Derived Hepatocyte Cells can be Used to Rescue Lethal Fulminant Hepatic Failure.

Materials and Methods

Animal Model.

To assess the therapeutic potential of iPSC-derived hepatocytes, a model of lethal fulminant hepatic failure caused by $CCl_4$ in NOD-SCID mice was used. A dose of 0.35 mL/kg body weight was optimal and resulted in lethality in all animals in 2 weeks after administration of $CCl_4$.

Five- to eight-week-old NOD-SCID mice were purchased from National Laboratory Animal Center (Taipei, Taiwan). All the experimental procedures involving the use of animals were approved by the Animal Care Committee of the Taipei Veterans General Hospital. The lethality of $CCl_4$ on NODSCID mice was tested by gavage. iPSC-derived hepatocyte cell transplants were performed at 24 hours after administration of $CCl_4$ by intrasplenic injection, as previously reported (Kuo T K, et al. *Gastroenterology* 134: 2111-2121, 2008).

Results

Figure 6A:
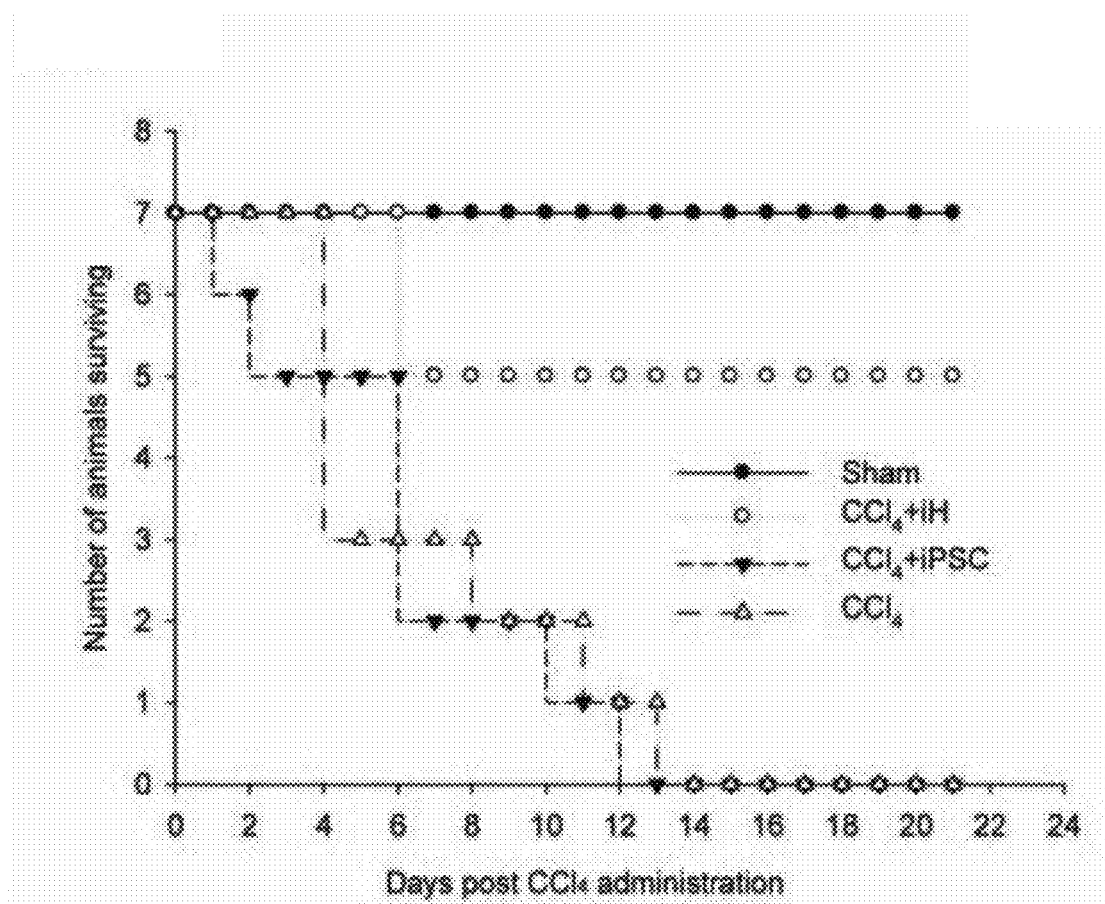
FIG. 6(A) depicts survival curves of NOD-SCID mice (n=7 in each group) that received intrasplenic cell transplantation with $4.0 \times 10^7$ iPSC-derived hepatocytes per kilogram body weight.
Figure 6B:
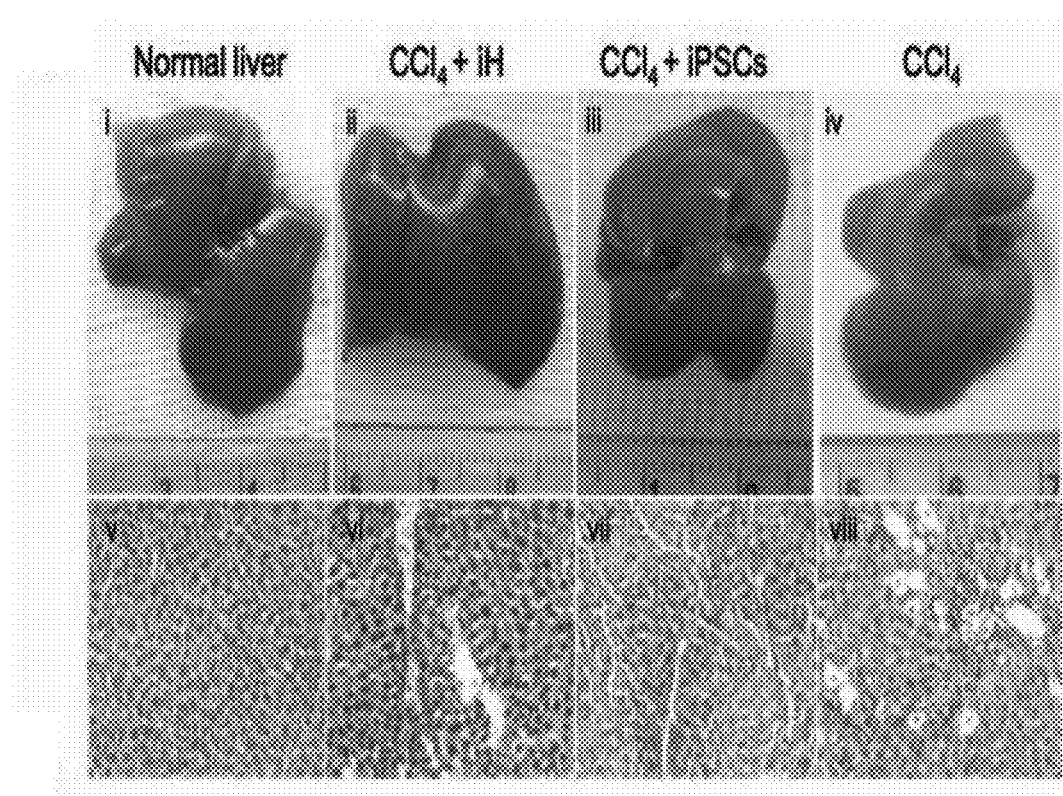
FIG. 6(B) depicts the appearance and histopathology of liver showing the organs with or without received cell transplantation (iPSC-derived hepatocytes or iPSCs) after administration of $CCl_4$ (Panels i and v=normal liver; Panels ii and vi=iPSC-derived hepatocytes transplanted after administration of $CCl_4$; Panels iii and vii=iPSCs transplanted after administration of $CCl_4$; Panels iv and viii=intrasplenic saline injection after administration of $CCl_4$).
Figure 6C:
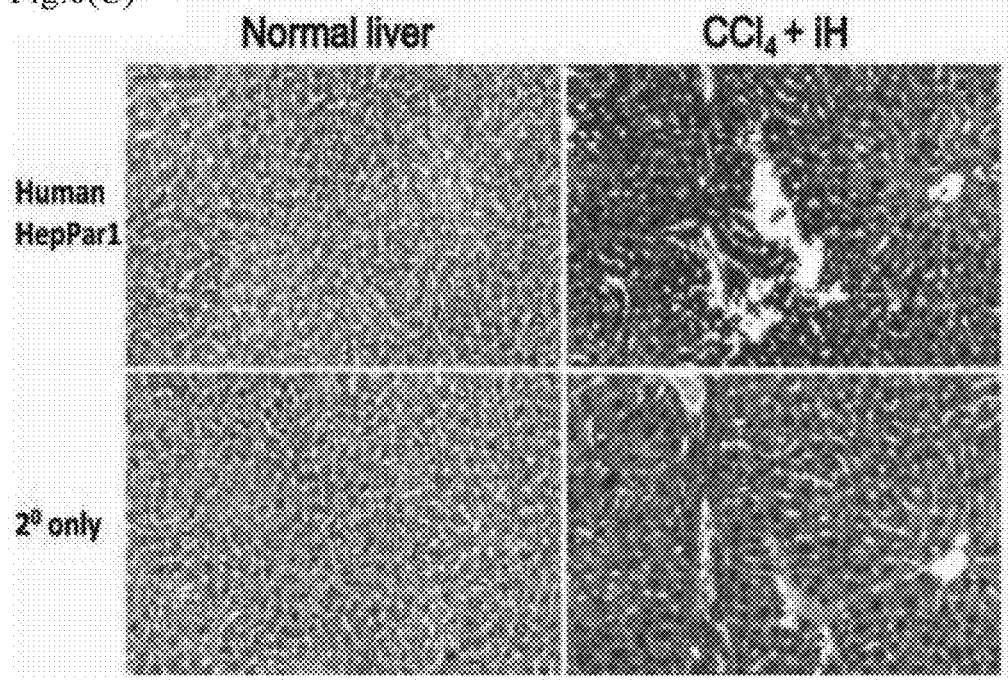
FIG. 6(C) and FIG. 6(FIG. 6D) show the detection of human hepatocytes with anti-human HepPar1 and human albumin antibodies with immunohistochemistry. (Original magnification, ×200).
Figure 6D:
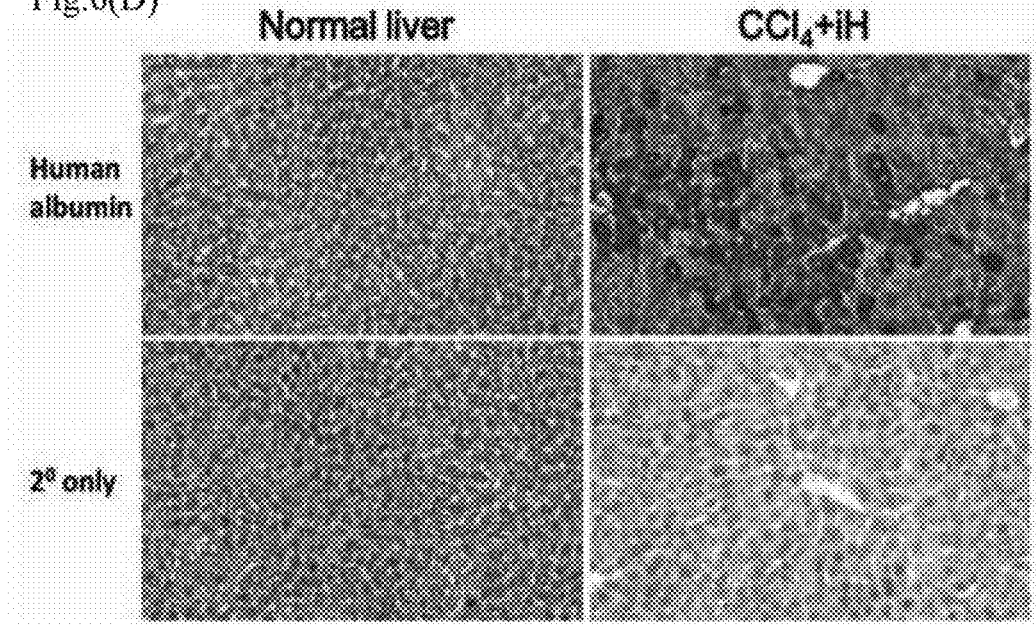

Transplantation of $4.0 \times 10^7$ iPSCs per kilogram body weight failed to rescue recipient animals from fulminant hepatic failure (0 of 7 mice survived). However, in mice that received iPSC-derived hepatocyte cells, 71% of the animals were rescued from the transplantation of $4.0 \times 10^7$ iPSC-derived hepatocytes per kilogram body weight (5 of 7 mice survived) (FIG. 6(A)). Histopathologic analysis showed the presence of submassive hepatic necrosis liver in mice (FIG. 6(B), panel viii), whereas the hepatic necrosis was rescued by transplantation of iPSC-derived hepatocytes, but not by iPSCs. Biochemical assays showed a dynamic change in the serum levels of hepatic marker proteins such as serum glutamyl oxaloacetic aminotransferase, glutamyl pyruvic aminotransferase, albumin, total bilirubin, and lactate dehydrogenase, confirming the infliction of acute liver failure by $CCl_4$ (Table 3).

TABLE 3

Liver function test of NOD-SCID mice that were administered 0.35 mL/kg $CCl_4$ and intrasplenic transplantion of iPSC-derived hepatocyte cells.

| | Serum glutamyl oxaloacetic aminotransferase (IU/L) | Glutamyl pyruvic aminotransferase (IU/L) | Albumin (g/dL) | Total bilirubin (mg/dL) | Lactate dehydrogenase (IU/L) |
|---|---|---|---|---|---|
| Normal NOD-SCID | 60 ± 6.6 | 34 ± 5.8 | 2.5 ± 0.11 | 0.4 ± 0.08 | 336 ± 14.5 |
| Post-$CCl_4$ day 1 | | | | | |
| Placebo | >1000 | >1000 | 3.4 ± 0.22 | 1.7 ± 0.23 | >4000 |
| iH-CT | >1000 | >1000 | 3.4 ± 0.16 | 1.7 ± 0.11 | >4000 |
| Post-$CCl_4$ day 3 | | | | | |
| Placebo | 513 ± 29.6 | 536 ± 93.2 | 3.2 ± 0.17 | 1.6 ± 0.10 | 3738 ± 123.8 |
| iH-CT | 191 ± 57.2 | 128 ± 24.0 | 2.7 ± 0.19 | 0.6 ± 0.43 | 427 ± 31.8 |
| Post-$CCl_4$ day 7 | | | | | |
| Placebo | 681 ± 31.6 | 557 ± 54.3 | 3.2 ± 0.08 | 1.7 ± 0.17 | 3754 ± 89.5 |
| iH-CT | 71 ± 12.9 | 39 ± 10.2 | 2.6 ± 0.12 | 0.4 ± 0.08 | 467 ± 41.3 |
| Post-$CCl_4$ day 14 | | | | | |
| Placebo | ND | ND | ND | ND | ND |
| iH-CT | 70 ± 8.9 | 45 ± 8.2 | 2.6 ± 0.04 | 0.4 ± 0.13 | 407 ± 20.2 |
| Post-$CCl_4$ day 21 | | | | | |
| Placebo | ND | ND | ND | ND | ND |
| iH-CT | 70 ± 4.6 | 44 ± 6.3 | 2.6 ± 0.09 | 0.5 ± 0.06 | 451 ± 37.0 |
| Post-$CCl_4$ day 28 | | | | | |
| Placebo | ND | ND | ND | ND | ND |
| iH-CT | 76 ± 4.2 | 43 ± 7.6 | 2.6 ± 0.12 | 0.4 ± 0.09 | 435 ± 49.0 |

Abbreviations: iH-CT; iPSC-derived hepatocyte cell transplantion; ND, not done.

To investigate whether the transplanted cells were engrafted in liver parenchyma of the recipients, two human hepatocyte-specific markers, HepPar1 and albumin, were used to detect human liver cells in mouse liver. Recipient mice that were rescued by intrasplenic transplantation of iPSC-derived hepatocytes were sacrificed on day 28 after transplantation. The immunohistochemical staining showed the presence of human HepPar1 and albumin in the liver parenchyma of recipient animals. These data indicate that the human iPSC-derived hepatocytes had been engrafted in recipient liver parenchyma (FIG. 6(C, D)).

Discussion

In this invention, a novel three-step process that efficiently generated hepatocyte-like cells from human iPSCs in vitro was developed. During the differentiation process, human iPSCs are exposed to a high level of activin, Wnt signaling, and HGF in a manner that is designed to mimic events during embryonic development in order to allow definitive endoderm formation. This is followed by a hepatic lineage commitment and a maturation step. The results show that it is successful to generate iPSC-derived hepatocyte cells that not only express hepatic markers but also have function of urea production and can carry out glycogen storage. Although other methods for the hepatogenic differentiation of human iPSCs have been described, few have shown a close relationship between the iPSC-derived hepatocyte cells and primary human hepatocytes, using microarray gene expression profiling. A comparison of the gene expression profile with that of a previous study showed that the differentiated cells of present invention have a similar gene profile to the earlier study, and that their profile is closely related to primary human hepatocytes.

During the endodermal induction step, morphology of the iPSCs changed from clustered to scattered with no cell-cell contact. Compared with cells cultured in media without HGF, we found that the presence of HGF may have a synergistic effect with activin A and Wnt3a and is able to efficiently drive iPSCs toward a definitive commitment to endoderm formation. Although several studies have demonstrated that HGF exerts several functions during angiogenesis and tumor progression, the role of HGF in embryonic development remains poorly understood. It has been previously reported that HGF induces a scattering of epithelial cells by up-regulating the expression of Snail, which is a transcription factor that controls the epithelial-to-mesenchymal transition. According to our findings, HGF induces a rapid increase in the expression of the definitive endoderm markers, Sox17 and Foxa2. The cell morphology of the iPSC also quickly changes into a spiky shape. Furthermore, the transcription factor Snail, which is a strong repressor of transcription of the E-cadherin gene, is up-regulated by the endodermal induction medium containing HGF, but not by medium without HGF (data not shown). Therefore, further analysis of the molecular mechanism related to HGF activities during early embryonic development is important to controlling hepatic lineage formation.

Using our differentiation process, it is possible to bring about the rapid and efficient generation of mature cells that exhibit characteristics of functional hepatocytes. The cytochrome P450 enzymes are critical enzymes associated with drug metabolism and the general metabolism of the human liver. The iPSC-derived hepatocyte cells expressed detectable enzyme activity for CYP3A4, which is the most important of the cytochrome P450s. This suggests strongly that these differentiated cells have the potential to be applied during in vitro model drug screening.

The in vitro differentiation system described in this specification allows the differentiation of hepatocyte cells has numerous advantages. First, it is possible to use these cells to treat liver diseases. This is because the method creates functional hepatocyte cells from human iPSCs, and these iPSC-derived hepatocyte cells can be reprogrammed from patient somatic cells. Second, the process is very rapid and highly efficient. Using our system, the differentiation of human iPSCs into functional hepatocyte-like cells requires only 12 days. This will facilitate the development of therapeutic protocols.

In conclusion, the disclosure herein has shown that human iPSCs can be directed to differentiate into mature hepatocyte cells in a rapid and efficient manner, through use of a three-step protocol as described. According to the gene expression pattern and functional analysis of the iPSC-derived hepatocyte cells, this invention has advanced the hepatogenic differentiation field. Furthermore, using the differentiated cells as a source of hepatocytes should help the development of alternative methods that may supersede liver transplantation when patients have liver failure. The method of present invention also offers the possibility of using the iPSC-derived hepatocyte cells for toxicity screening during drug discovery.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. An in vitro differentiation process for generating mature hepatocytes from human induced pluripotent stem cells in less than 20 days, which comprises the steps of:
   (a) culturing human induced pluripotent stem cells (iPSCs) in MEF-conditioned medium comprising Dulbecco's modified Eagle medium (DMEM)/F12 supplemented with 20% knockout serum replacement, 10 ng/mL basic fibroblast growth factor, 1 mM L-glutamine, 100 µM nonessential amino acids, 100 µM 2-mercaptoethanol, 50 U/mL penicillin, and 50 mg/mL streptomycin to 70% confluence;
   (b) replacing the MEF-conditioned medium with culture medium containing 100 ng/mL activin A, 50 ng/mL wingless-type MMTV integration site family, member 3A (Wnt3a) and 10 ng/mL hepatocyte growth factor (HGF), and culturing the cells for 3-5 days;
   (c) replacing the culture medium with hepatic commitment medium comprising knockout [KO]/DMEM containing 20% knockout serum replacement, 1 mM L-glutamine, 1% nonessential amino acids, 0.1 mM 2-mercaptoethanol, and 1% dimethyl sulfoxide, and culturing the cells for 4-6 days; and
   (d) culturing cells from c) in Iscove's modified Dulbecco's medium (IMDM) containing 20 ng/mL oncostatin M, 0.5 µM dexamethasone, and 50 mg/mL insulin, transferrin, selenous acid (ITS) premix for 5-7 days to obtain differentiated hepatocytes; wherein said differentiated hepatocytes (i) exhibit gene expression profile similar to mature hepatocytes, and (ii) have function of urea production and glycogen storage.

2. The process of claim 1, wherein the human iPSCs are growing in feeder-free culture conditions for 4-6 days before the hepatogenic differentiation, and the human iPSCs exhibit pluripotent properties.

3. The process of claim 1, wherein the differentiated hepatocyte cells are competent for LDL uptake.

* * * * *